United States Patent [19]
Arnold

[11] Patent Number: 5,961,529
[45] Date of Patent: Oct. 5, 1999

[54] HOURGLASS-SHAPED DERMAL PUNCH AND METHODS FOR ITS USE

[76] Inventor: James E. Arnold, 24142 Big Basin Way, Saratoga, Calif. 95070

[21] Appl. No.: 09/005,745

[22] Filed: Jan. 12, 1998

[51] Int. Cl.$^6$ ..................................................... A61B 17/00
[52] U.S. Cl. ............................................................ 606/133
[58] Field of Search ........................... 606/133, 184–188; 600/564–568

[56] References Cited

U.S. PATENT DOCUMENTS 5,183,053  2/1993  Yeh et al. ................................ 606/167
5,792,163  8/1998  Hitzig ....................................... 606/184

*Primary Examiner*—Michael Buiz
*Assistant Examiner*—William Lewis
*Attorney, Agent, or Firm*—Townsend and Townsend and Crew LLP

[57] ABSTRACT

The invention provides an exemplary dermal punch and methods for its use. The dermal punch comprises a handle and a tubular shaft having a proximal end and a distal end. The proximal end is operably attached to the handle and the distal end is sharpened and has a generally hourglass shape.

5 Claims, 4 Drawing Sheets

Fig. 1
(Prior Art)
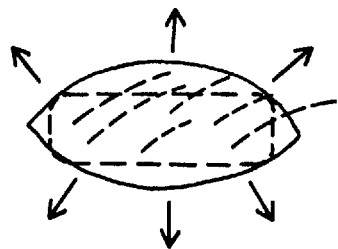
Fig. 2
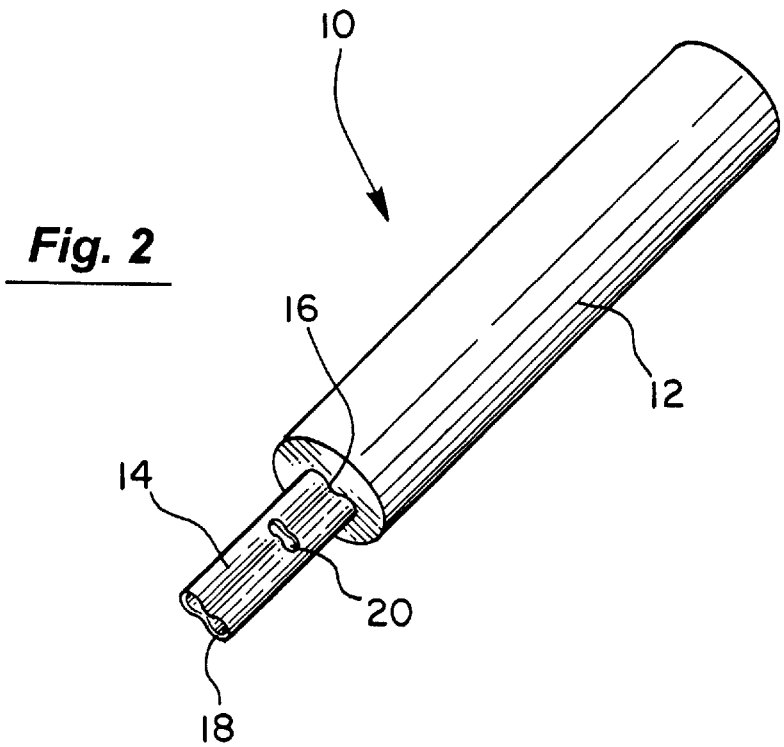
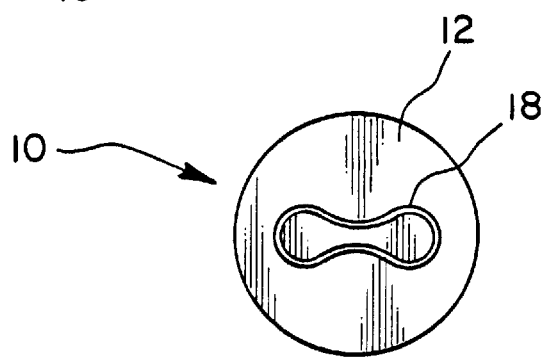
Fig. 3

HOURGLASS-SHAPED DERMAL PUNCH AND METHODS FOR ITS USE

BACKGROUND OF THE INVENTION

The invention relates generally to the field of hair transplantation, and in particular to the placement of grafts of skin having hair into previously formed incisions in the scalp. In one particular aspect, the invention relates to the formation of incisions which match the size and shape of the skin graft.

One method of hair transplantation currently in use includes the step of obtaining long, narrow strips of a hair-bearing donor scalp. The strips generally vary in width between about 2 mm and 5 mm, with 3 mm being the usual width of choice. Such strips are cut about every 1 mm along their lengths to produce 1 mm by 3 mm rectangular pieces of hair-bearing scalp, often referred to as grafts.

One common method for placing the rectangular pieces of hair-bearing scalp into bald areas is by making a slit incision in the skin approximately 3 mm long. Although no tissue is removed by the simple incision, the natural tension of the skin pulls the incision open, producing a fusiform opening as illustrated in FIG. 1. The rectangular graft is then inserted into the fusiform opening as shown in FIG. 1.

Since the fusiform opening is larger in size than the graft of skin that is transplanted, undesirable scar tissue will develop. Further, since there is little contact between the bald scalp and the hair-bearing transplant, the healing process and the chance of survival are hindered. Moreover, since no skin tissue is removed from the bald scalp, as multiple grafts are transplanted, the scalp in the region of the transplant will have excessive skin tissue.

Instead of using a simple slit, some have proposed the use of an elliptical punch that is used to remove a piece of the bald scalp. However, due to the natural skin tension, the central section of the opening will broaden into an oval shape. As such, the incision will be larger than the graft, which will promote the growth of scar tissue, reduce the healing process, and reduce the chance of survival.

Hence, it would be desirable to provide a device and method which would facilitate the transplantation of generally rectangular pieces of hair-bearing scalp into a bald region of the scalp. It would be particularly desirable if the opening in the skin matched the size and shape of the skin graft so that the healing process and chance of survival could be improved. It would be further desirable if such a device and method reduced the formation of scar tissue to produce a more aesthetically appealing hair transplant.

SUMMARY OF THE INVENTION

The invention provides an exemplary dermal punch and methods for its use which overcome or greatly reduce the drawbacks associated with prior art hair transplantation procedures. In one exemplary embodiment, a dermal punch is provided which comprises a handle and a tubular shaft having a proximal end and a distal end. The proximal end is operably attached to the handle and the distal end is sharpened and has a generally hourglass shape. By employing an hourglass shape, the dermal punch takes advantage of the natural tension of the skin to produce generally rectangular incisions to facilitate the receipt of a generally rectangular graft of skin. In particular, once an hourglass-shaped piece of skin is removed by the punch, the natural tension of the skin around the incision pulls the central portion of the incision outward to form a generally rectangular opening.

The hourglass shape will preferably be defined by two outer regions and an inner region. The outer regions will preferably have a width in the range from about 2 mm to about 0.5 mm, and more preferably about 1 mm, and the width of the inner region will preferably be in the range from about 1.5 mm to about 0.015 mm, and more preferably about 0.5 mm. The length spanning the two outer regions and the inner region will preferably be in the range from about 2 mm to about 5 mm, and more preferably at about 3 mm.

In one particular aspect, the tubular shaft is preferably constructed of stainless steel. In another aspect, the tubular shaft preferably includes a tissue escape port between the proximal and distal ends to allow accumulated tissue to escape from the shaft.

The invention further provides an exemplary method for transplanting grafts of skin having hair. The method comprises obtaining a generally rectangular graft of skin having at least one hair. A generally hourglass-shaped incision is formed in the scalp, and a section of skin defined by the incision is removed to create a region for receiving the graft of skin. The graft of skin is then placed into the region.

After producing the hourglass-shaped incision, the natural tension of the skin in the vicinity of incision will expand the region into a generally rectangular geometry. In this way, the region will match the shape of the graft.

The incision is preferably formed by inserting a distal end of a tubular shaft into the scalp, with the distal end being sharpened and having a generally hourglass shape. During a procedure, a plurality of generally hourglass-shaped incisions will preferably be formed in the scalp so that a graft of skin having at least one hair may be placed into each incision.

BRIEF DESCRIPTION OF THE DRAWINGS

FIG. 1 illustrates a prior art method for transplanting a generally rectangular graft of skin into a fusiform opening.

FIG. 2 is a perspective view of an exemplary dermal punch having a generally hourglass-shaped distal end according to the invention.

FIG. 3 is a bottom view of the dermal punch of FIG. 2.

DETAILED DESCRIPTION OF THE SPECIFIC EMBODIMENTS

Figure 4:
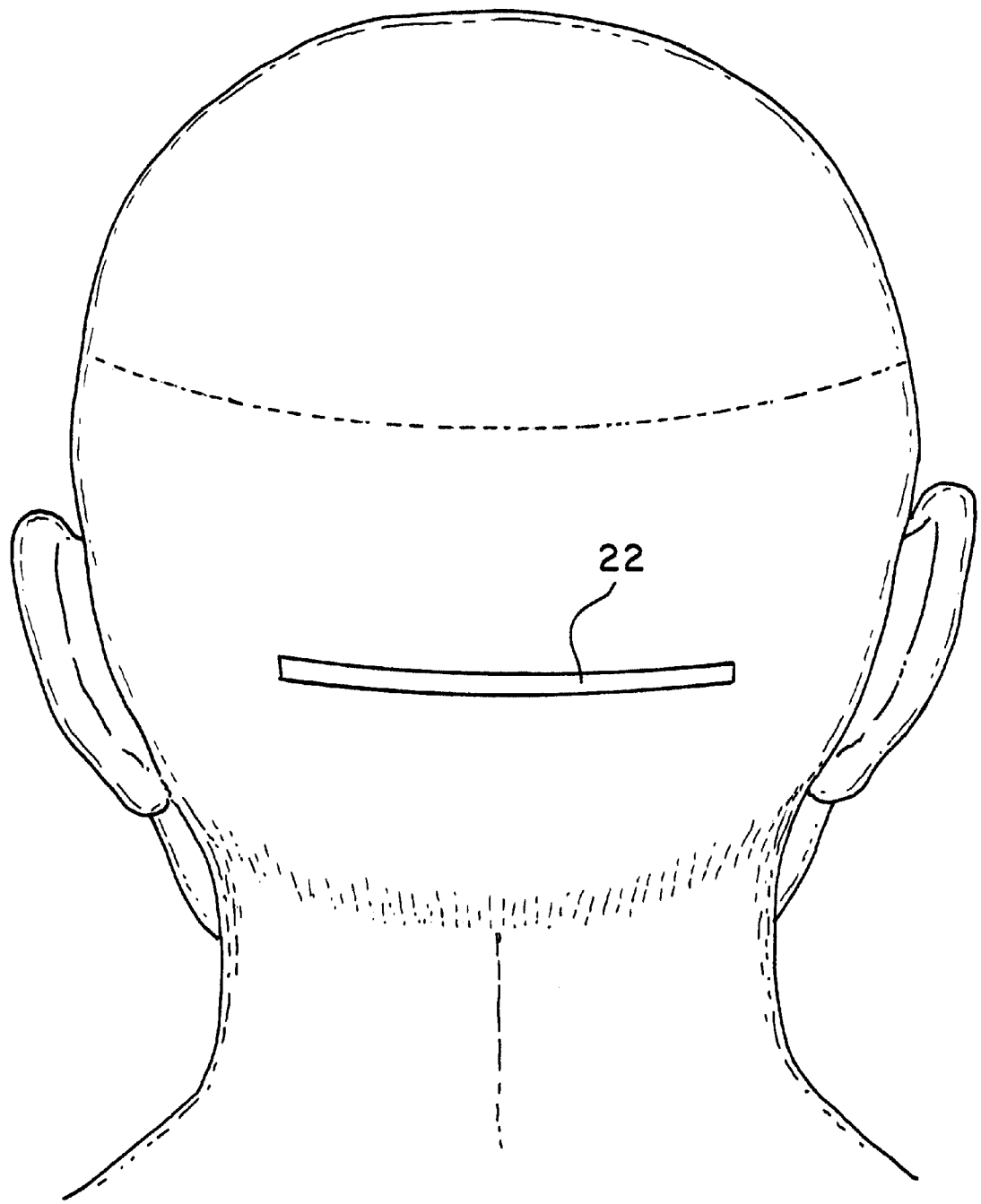
FIG. 4 illustrates the removal of a donor strip of scalp during a hair transplantation procedure according to the invention.

The invention provides an exemplary dermal punch and methods for its use to facilitate the transplantation of generally rectangular grafts of skin having hair into bald areas of the scalp. Exemplary procedures for producing donor strips, operating dermal punches, and placing grafts into the scalp are described generally in U.S. Pat. No. 5,611,810 and in co-pending U.S. application Ser. Nos. 08/375,314, filed Jan. 18, 1995; 08/375,313, filed Jan. 18, 1995; and 08/789,970, filed Jan. 31, 1997. The disclosures of all these references are herein incorporated by reference.

Referring now to FIG. 2, an exemplary embodiment of a dermal punch 10 will be described. Dermal punch 10 comprises a handle 12 and a tubular shaft 14 having a proximal end 16 and a distal end 18. Proximal end 16 is operably attached to handle 12. Handle 12 may be constructed of materials such as plastics, metals, and the like, and will be configured to securely receive proximal end 16. Tubular shaft 14 is preferably constructed of stainless steel and is fashioned such that it has a cross-sectional geometry in the general shape of an hourglass as illustrated in FIG. 3. Distal end 16 is also sharpened so that it may penetrate the scalp when pressed therein. Formed within tubular shaft 14 is a tissue escape port 20 which allows accumulated tissue to escape from tubular shaft 14 during a hair transplantation procedure.

Figure 5:
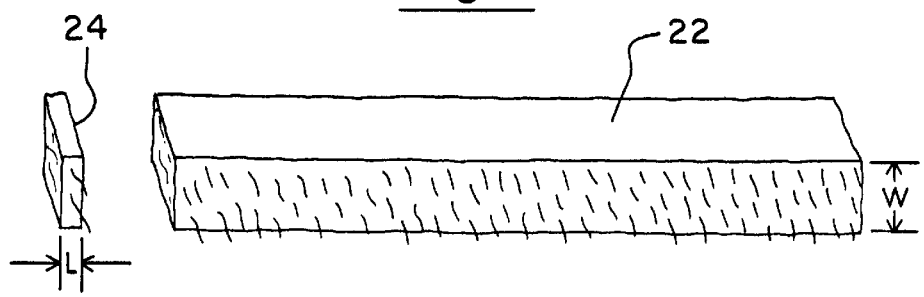
FIG. 5 is a detailed view of the donor strip of FIG. 4 with a generally rectangular graft having been removed in preparation of its transplant into the scalp.

An exemplary procedure for transplanting grafts of skin having hair into bald regions of the scalp will now be described with reference to FIGS. 4–9. As illustrated in FIG. 4, two or more elongate slits are made in a hair-bearing region of the scalp to produce one or more donor strips 22. Donor strips 22 are then removed from the scalp as illustrated in FIG. 5. Donor strips 22 will preferably have a width W that is in the range from about 2 mm to about 5 mm, and more preferably about 3 mm. Pieces or grafts 24 are then separated from donor strip 22 as illustrated in FIG. 5. Preferably, graft 24 will have a length L that is in the range from about 2.0 mm to about 0.5 mm, and more preferably about 1 mm. In this way, a plurality of generally rectangular grafts are produced for transplantation into a bald area of the scalp.

Figure 6:
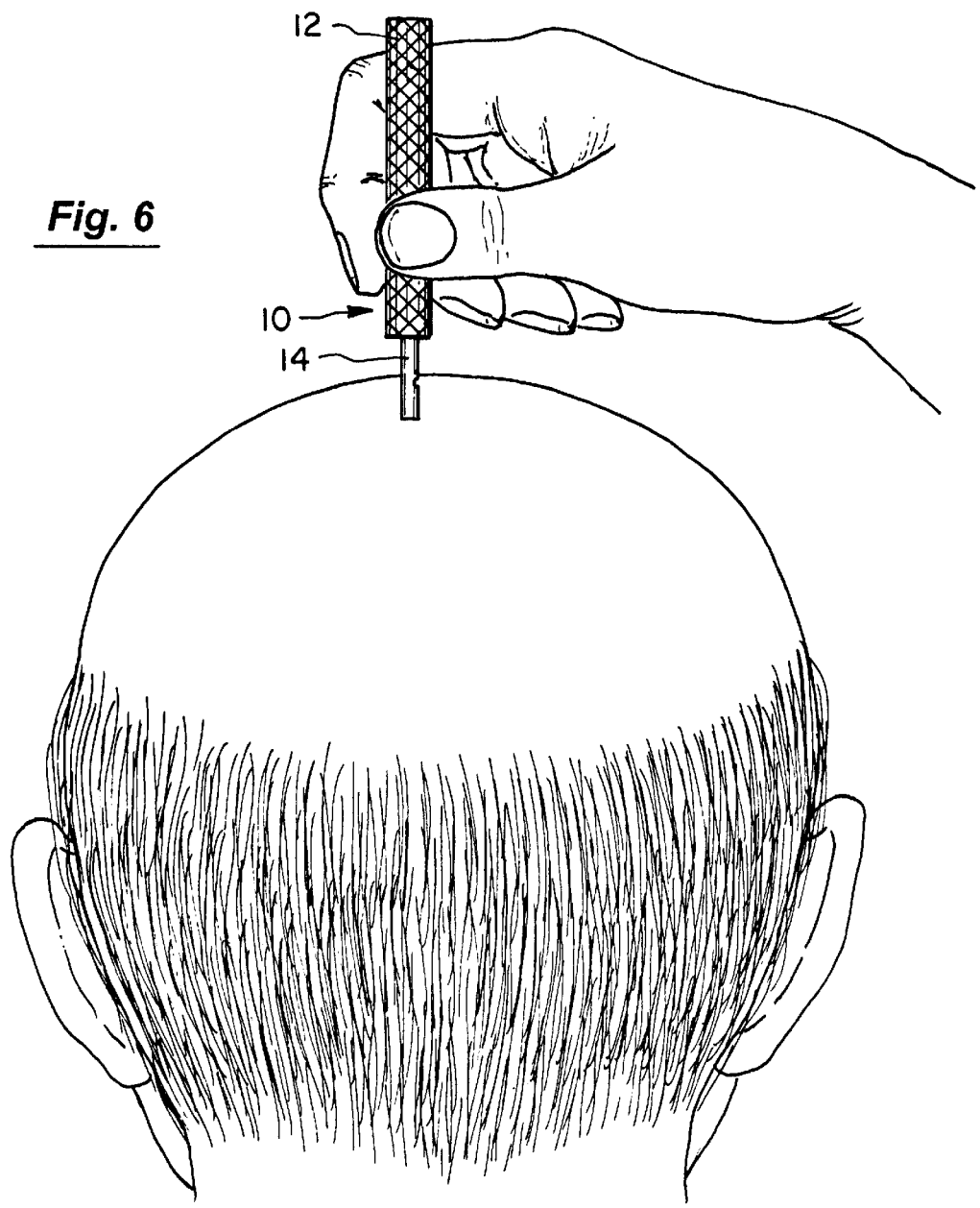
FIG. 6 illustrates the dermal punch of FIG. 2 being inserted into the scalp during a hair transplantation procedure.
Figure 7:
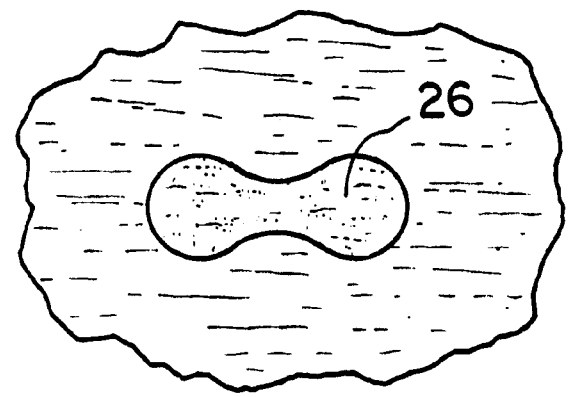
FIG. 7 illustrates the hourglass-shaped incision formed by the dermal punch when inserted into the scalp as illustrated in FIG. 6.

As illustrated in FIG. 6, dermal punch 10 is then pressed into the scalp at one or more locations to prepare the scalp for receiving grafts 24. When distal end 18 is pressed into the scalp, a generally hourglass-shaped incision 26 is produced as illustrated in FIG. 7. As distal end 18 is removed from the scalp, the skin within incision 26 will be removed by tubular shaft 14. If the plug of tissue is not removed, a pair of tweezers may be employed to remove the hourglass-shaped plug of tissue.

The hourglass-shaped incision 26 has two outer regions and a central inner region. The outer regions will preferably have a width in the range from about 2.0 mm to about 0.5 mm, and more preferably about 1 mm, and the width of the inner region will preferably be in the range from about 1.5 mm to about 0.25 mm, and more preferably about 0.5 mm. The length spanning the two outer regions and the inner region will preferably be in the range from about 2 mm to about 5 mm, and more preferably at about 3 mm.

Figure 8:
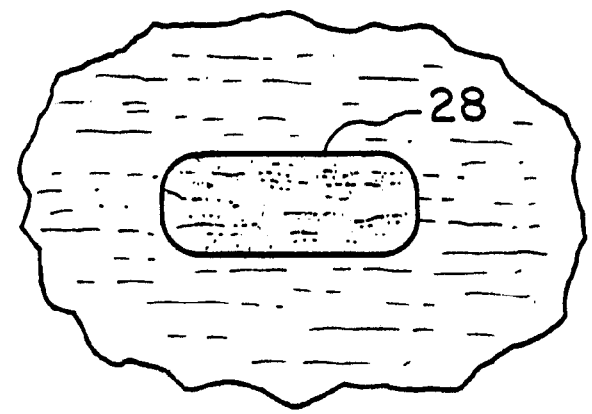
FIG. 8 illustrates the incision of FIG. 7 after the natural tension of the skin has expanded the incision into a generally rectangular geometry.

After forming the generally hourglass-shaped incision, the natural tension of the skin moves the central region of the incision outward to form a generally rectangular incision 28 as illustrated in FIG. 8. Graft 24 is then inserted into incision 26 as illustrated in FIG. 9.

Figure 9:
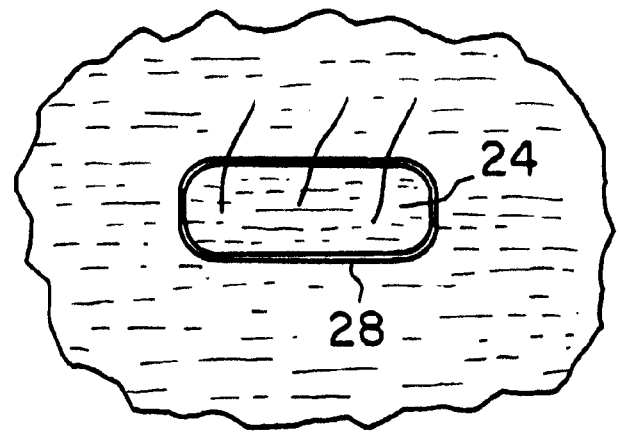
FIG. 9 illustrates the incision of FIG. 8 having received a graft of skin according to the invention.

As illustrated in FIG. 9, incision 26 is generally of the same geometry and size as is graft 24. In this way, the generation of scar tissue will be greatly reduced. Further, since the contact between the bald scalp and transplant 24 is maximized, the healing process will be greatly increased as well as the chance of survival.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A method for transplanting grafts of skin having hair, the method comprising:

obtaining a generally rectangular graft of skin having at least one hair;

forming a generally hour glass shaped incision in the scalp;

removing a section of skin defined by the incision to create a region for receiving the graft of skin;

placing the graft of skin into the region.

2. A method as in claim 1, further comprising allowing the natural tension of the skin in the vicinity of the incision to expand the region into a generally rectangular geometry prior to placing the graft of skin into the region.

3. A method as in claim 1, further comprising forming the incision by inserting a distal end of a tubular shaft into the scalp, wherein the distal end is sharpened and has a generally hourglass shape.

4. A method as in claim 3, further comprising removing accumulated tissue from the tubular shaft through a tissue escape port in a wall of the shaft.

5. A method as in claim 1, further comprising forming a plurality of generally hour glass shaped incisions in the scalp and placing a graft of skin having at least one hair into each incision.

* * * * *